United States Patent [19]
Keil et al.

[11] Patent Number: 5,833,968
[45] Date of Patent: *Nov. 10, 1998

[54] AQUEOUS COMPOSITION FOR FIXING HAIR IN THE FORM OF A HIGH VISCOUS SPRAYABLE GEL

[75] Inventors: Wolfgang Keil, Mühlheim; Jürgen Schmenger, Weiterstadt; Bernd Stein, Hösbach, all of Germany

[73] Assignee: Wella Aktiengesellschaft, Darmstadt, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 374,667
[22] PCT Filed: May 4, 1994
[86] PCT No.: PCT/EP94/01422
  § 371 Date: Jan. 20, 1995
  § 102(e) Date: Jan. 20, 1995
[87] PCT Pub. No.: WO95/00104
  PCT Pub. Date: Jan. 5, 1995

[30] Foreign Application Priority Data

Jun. 23, 1993 [DE] Germany .......................... 43 20 797.9

[51] Int. Cl.⁶ .............................. A61K 7/11; A61K 47/32; A61K 47/36; A61K 47/46
[52] U.S. Cl. ..................................... 424/70.17; 424/70.16; 424/70.15; 424/70.13; 424/74; 424/DIG. 1; 424/DIG. 2; 424/195.1; 514/783
[58] Field of Search ................................ 424/70.1, 70.16, 424/70.17, 70.15, 70.13, 74, DIG. 2, DIG. 1, 195.1; 514/783

[56] References Cited

U.S. PATENT DOCUMENTS

5,266,303  11/1993  Myers et al. .............................. 424/47

*Primary Examiner*—Edward J. Webman
*Attorney, Agent, or Firm*—Michael J. Striker

[57] ABSTRACT

The aqueous hair fixing composition is in the form of a highly viscous sprayable gel and contains 0.1 to 50 percent by weight of one or more disaccharides or a mixture of 2 to 37 percent by weight of one or more disaccharides and 63 to 98 percent by weight of one or more oligosaccharides, 0.05 to 30 percent by weight of one or more cationic polymers, and 0.05 to 10 percent by weight of at least one thickener selected from the group consisting of honopolymers of acrylic acid, acrylic acid/acrylamides copolymers and sclerotium gum, The composition of the invention necessarily does hot contain monovalent aliphatic alcohols having 1 to 4 carbon atoms and no inorganic salts of alkali metals or inorganic salts of bivalent or trivalent metals. Either the composition is sprayed with the aid of a mechanical spray device or, alternatively, a gaseous propellant is included in it and the composition and propellant is included under pressure in a dispensing container.

29 Claims, No Drawings

AQUEOUS COMPOSITION FOR FIXING HAIR IN THE FORM OF A HIGH VISCOUS SPRAYABLE GEL

This application is a continuation under 35 U.S.C. 371 of PCT/EP94/01422, filed May 4, 1994.

BACKGROUND OF THE INVENTION

The subject of the present invention is an aqueous composition for fixing hair in the form of a highly viscous sprayable gel which contains a combination of at least one disaccharide or a disaccharide and an oligosaccharide with a cationic polymer and a thickener and has no monovalent aliphatic alcohols with 1 to 4 carbon atoms and determined salts.

At present, along with the conditioning and cleaning of hair, increasing importance is placed on shaping or hairstyling. In this respect, a distinction must be drawn between permanent and temporary hair-shaping.

Permanent shaping involves chemical action in the structure of the hair with the use of permanent wave compositions, whereas in temporary shaping, compositions whose essential constituents are film-forming polymers are used for fixing hair.

Film-forming polymers are conventionally used in alcoholic or aqueous-alcoholic solution in hair fixing compositions, foam fixing compositions, hair sprays and fixing gels.

The greatest disadvantages of known gel formulations are the poor proportioning and distributing properties of these gels, which are normally dispensed from tubes, and the intensive loading of hair associated with these gels.

This poses the problem of finding a hair fixing composition in gel form which provides good fixing of the hair and is easy to proportion and distribute in the hair.

SUMMARY OF THE INVENTION

Surprisingly, it has now been found that this problem is solved in an outstanding manner by an aqueous composition for fixing hair in the form of a highly viscous sprayable gel which contains a combination of a disaccharide or a mixture of a disaccharide and an oligosaccharide with a cationic polymer and a thickener and is free of monovalent aliphatic alcohols with 1 to 4 carbon atoms and certain inorganic salts.

Therefore, the subject of the present invention is an aqueous hair fixing composition in the form of a highly viscous sprayable gel containing a) 0.1 to 50 percent by weight of at least one disaccharide or a mixture of 2 to 37 percent by weight of at least one disaccharide and 63 to 98 percent by weight of at least one oligosaccharide, b) 0.05 to 30 percent by weight of at least one cationic polymer and c) 0.05 to 10 percent by weight of at least one thickener and which contains d) no monovalent aliphatic alcohols with 1 to 4 carbon atoms and e) no inorganic salts of alkali metals or inorganic salts of bivalent or trivalent metals.

The highly viscous sprayable gel according to the invention preferably has a viscosity of 200 to 10,000 m Pa.s (milli-pascal seconds), in particular preferably 500 to 6,000 m Pa.s. The viscosity of the gel according to the invention was measured by a Haake viscosimeter VT 501 at 25° C. and a SV-DIN shear rate of 12.9 $s^{-1}$ (row B, position 5).

Although it takes the form of a high-viscosity gel, the composition according to the invention can be sprayed with a conventional mechanical spraying device (e.g., a spray pump) or with a propellant from a conventional aerosol pressurized container with a conventional spray head as a finely distributed gel.

Since it may be sprayed, the composition according to the invention can be proportioned precisely and distributed uniformly in hair. The polymer film produced on the hair by the composition according to the invention is resilient and resistant to moisture in the air.

The composition according to the invention has a very good fixing action and may be washed out of hair easily. Surprisingly, in spite of the saccharide content in the composition according to the invention, hair which has been treated with the composition according to the invention does not have a sticky feel. Moreover, the composition according to the invention has none of the monovalent aliphatic alcohols with 1 to 4 carbon atoms which are contained in conventional compositions for fixing hair.

Saccharide-containing hair treatment compositions are known, for example, from DE-OS 34 04 627. The described compositions preferably take the form of lotions and necessarily contain salts. DE-OS 34 04 627 does not suggest providing a hair fixing composition in the form of a highly viscous sprayable gel which can be favorably proportioned and distributed easily and uniformly.

In the present invention, oligosaccharides are understood as saccharides with 3 to 6 monosaccharides connected in the manner of acetal compounds.

DESCRIPTION OF THE PREFERRED EMBODIMENTS

The disaccharide/oligosaccharide mixtures which can be contained in the composition according to the invention as component a) are preferably mixtures of glucose disaccharides and glucose oligosaccharides such as those sold by Cerestar, Krefeld, Germany, under the trade name C-Pur®. In particular, the composition according to the invention preferably contains, as component a), maltose or the glucose disaccharide/glucose oligosaccharide mixture sold by Cerestar, Krefeld, Germany, under the trade name C-Pur® 01924.

The composition according to the invention preferably contains 1 to 25 percent by weight of component a).

The cationic polymers contained in the composition according to the invention as component b) are preferably polyvinylpyrrolidone/dimethylaminoethyl methacrylate polymers. In a particularly preferred embodiment, the composition according to the invention contains the polyvinylpyrrolidone/dimethylaminoethyl methacrylate copolymer sold by Gaf Co., New York, U.S.A., under the trade name Gafquat® 755N. Other examples of cationic polymers are the copolymer of polyvinylpyrrolidone and imidazoliminmethochioride sold by BASF AG, Ludwigshafen, Germany, under the trade name Luviquat® H11 550, the terpolymer of dimethyl diallyl ammonium chloride, sodium acrylate and acrylamide sold by Calgon, Pittsburgh, U.S.A., under the trade name Merquat® Plus 3330, the terpolymer of vinylpyrrolidone, dimethylaminoethyl methacrylate and vinylcaprolactum sold by ISP, U.S.A., under the trade name Gaffix® VC 713, the quaternary ammonium salt of hydroxyethylcellulose and a trimethylammonium-substituted epoxide sold by Amerchol, Edison, U.S.A., under the trade name Polymer IR®, the vinylpyrrolidone/methacrylamidopropyltrimethyl ammonium chloride copolymer sold by Gaf Co., New York, U.S.A. under the trade name Gafquat® HS 100 and the diquaternary polydimethylsiloxane sold by Goldschmidt, Essen, Germany, under the trade name Abil® Quat 3272.

The composition according to the invention preferably contains 0.05 to 10 percent by weight of component b).

Preferred thickeners contained in the composition according to the invention as component c) are homopolymers of acrylic acid with a molecular weight of 2,000,000 to 6,000,000 such as those sold by B.F. Goodrich, Cleveland, U.S.A., under the trade name Carbopol®. In particular, the composition according to the invention preferably contains an acrylic acid homopolymer with a molecular weight of 4,000,000 such as that sold by B.F. Goodrich under the trade name Carbopol® 940. Other thickeners are, e.g., the acrylic acid homopolymers sold by B.F. Goodrich under the trade name Carbopol® ETD 2001 or by Protex, France, under the trade name Modarez V 600 PX, the polymer of acrylic acid and acrylamide (sodium salt) with a molecular weight of 2,000,000 to 6,000,000 sold by Hoechst, Germany, under the trade name Hostacerin PN 73® and the sclerotium gum sold under the trade name Amigel® by Alban Muller, Montreuil, France.

The composition according to the invention preferably contains 0.1 to 5 percent by weight of component c).

In addition, the composition according to the invention can contain 0.1 to 15 percent by weight, preferably 0.1 to 7 percent by weight, of at least one nonionic polymer. Preferred nonionic polymers which may be contained in the composition according to the invention are polyvinylpyrrolidone polymers such as those sold by BASF AG, Ludwigshafen, Germany, under the trade name Luviskol®. A particularly preferred polyvinylpyrrolidone polymer contained in the composition according to the invention is that sold by BASF AG under the trade name Luviskol® VA 64.

A naturally occurring nonionic polymer is hydroxypropyl chitosan, for example.

In addition, the composition according to the invention can contain 0.1 to 15 percent by weight, preferably 0.1 to 7 percent by weight, of at least one anionic polymer. In particular, anionic polymers preferably contained in the composition according to the invention are the sodium polystyrene sulfonate sold under the trade name Flexan® 130 by National Starch, Braunston, Great Britain, and the copolymer of methacrylic acid and methacrylate sold under the trade name Diahold® A 503 by Sandoz, Basel, Switzerland. Other anionic polymers include the terpolymer of polyvinylpyrrolidone, ethylmethacrylate and methacrylic acid sold by Stepan, Northfield, U.S.A., under the trade name Stepanhold® R-1 and the copolymer of methacryloyl ethyl betaine and methacrylate sold by Sandoz under the trade name Diaformer® Z 301 and shellac, e.g., Schellack MHP 210 available from Pennig, Germany.

The composition according to the invention preferably contains no organic solvents.

The composition according to the invention contains 20 to 98 percent by weight, preferably 50 to 96 percent by weight, water. The composition according to the invention has a pH of 4 to 9, preferably 6 to 8.

Of course, in addition to the ingredients mentioned above, the composition according to the invention can also contain conventional cosmetic additives such as perfume oils in quantities of approximately 0.1 to 5.0 percent by weight, opacifiers such as ethylene glycol distearate in quantities of approximately 0.5 to 5.0 percent by weight, pearlescing agents such as a mixture of fatty acid monoalkylolamide and ethylene glycol distearate in quantities of approximately 0.01 to 10.0 percent by weight, amines or alkanolamines suitable for neutralizing, e.g., 2-amino-2-methylpropanol, wetting agents or emulsifiers from the classes of anionic, cationic, amphoteric or nonionic surface-active substances such as fatty alcohol sulfates, ethoxylated fatty alcohol sulfates, alkyl sulfonates, alkyl benzene sulfonates, alkyl trimethylammonium salts, alkyl betaines, ethoxylated fatty alcohols, ethoxylated nonylphenols, fatty acid alkanolamides, glyceride alkoxylates, e.g., fatty acid esters of hydrated castor oil with ethoxylated glycerol in quantities of 0.01 to 15 percent by weight, as well as dyes such as fluorescein sodium salt in quantities of approximately 0.1 to 1.0 percent by weight, hair nurturing additives such as pantothenic acid in quantities of approximately 0.01 to 10 percent by weight, hair moisteners such as 1,2-propanediol and glycerol, dyes, lightfastness agents, antioxidants, brighteners such as sorbitol and preservatives such as p-hydroxybenzoic acid ester, sorbic acid, salicylic acid, mandelic acid or formic acid in quantities of 0.01 to 10 percent by weight.

If desired, the hair fixing composition according to the invention can be used to dye or tint hair at the same time when it contains cosmetic dyes. Such preparations are known commercially, for example, as dye fixing compositions or tint fixing compositions. They contain, in addition, conventional dyes which are absorbed directly in the hair, e.g. aromatic nitro dyes such as 1,4-diamnino-2-nitrobenzene, picramic acid, 1-N-hydroxyethylamino-4-methyl-2-nitrobenzene, 1-hydroxy-2-amino-4-nitrobenzene and 1,4-bis(2-hydroxyethyl)amino-2-nitro-5-chlorobenzene, azo dyes such as Acid Brown 4 (C.I. 14,805), anthraquinone dyes such as Disperse Violet 4 (C.I. 61,105) and triphenylmethane dyes such as Basic Violet I (C.I. 42,535), Basic Violet 14 (C.I. 42,510), Basic Red 76 (C.I. 12,245) or Basic Blue 7 (C.I. 42,595:1). Depending on their substituents, these dyes can have an acidic, nonionic or alkaline character. The total concentration of such dyes in the composition according to the invention is generally approximately 0.01 to 2.0 percent by weight.

The hair fixing composition according to the invention is preferably sprayed by a propellant or with the aid of a mechanically operated spraying device.

Lower alkanes such as n-butane, i-butane and propane, or mixtures of lower alkanes with dimethyl ether and other gaseous propellants, e.g. $N_2$, $N_2O$ and $CO_2$, at the appropriate pressures, as well as mixtures of the aforementioned propellants are suitable for use as propellants.

In particular, the hair fixing composition according to the invention is preferably sprayed with the aid of a mechanically operated spraying device.

By mechanically operated spraying device is meant devices which spray liquids without the use of propellants. For example, a suitable mechanical spraying device can be a spray pump or a flexible container which is provided with a spray valve and contains the cosmetic composition according to the invention under pressure. This flexible container expands and the composition can be dispensed in a continuous manner from this container due to the contraction of the flexible container by opening the spray valve.

The hair fixing composition according to the invention provides excellent fixing without a sticky feel and can be brushed out and washed out of hair easily. Since it can be sprayed by mechanical spraying devices or with the use of propellants, it is easy to proportion and distributed in the hair.

The following examples explain the subject matter of the invention in more detail.

EXAMPLES

Example 1

Gel spray with normal fixing

| | |
|---|---|
| 6.00 g | maltose |
| 0.06 g | polyvinylpyrrolidone/dimethylaminoethyl methacrylate copolymer (Gafquat ® 755 N, Gaf Co., U.S.A.) |
| 0.20 g | homopolymer of acrylic acid with a molecular weight of 4,000,000 (Carbopol ® 940, B. F. Goodrich, U.S.A.) |
| 0.23 g | 2-amino-2-methylpropanol |
| 0.10 g | perfume oil |
| 93.41 g | water |
| 100.00 g | |

Example 2

Gel spray with intensive fixing

| | |
|---|---|
| 8.00 g | mixture of glucose disaccharide and glucose oligosaccharide (C-Pur ® 01924, Cerestar, Germany) |
| 0.08 g | polyvinylpyrrolidone/dimethylaminoethyl methacrylate copolymer (Gafquat ® 755 N, Gaf Co., U.S.A.) |
| 0.22 g | homopolymer of acrylic acid with a molecular weight of 4,000,000 (Carbopol ® 940, B. F. Goodrich, U.S.A.) |
| 0.26 g | 2-amino-2-methylpropanol |
| 0.15 g | perfume oil |
| 91.29 g | water |
| 100.00 g | |

Example 3

Gel spray with extra-intensive fixing

| | |
|---|---|
| 10.00 g | mixture of glucose disaccharide and glucose oligosaccharide (C-Pur ® 01924, Cerestar, Germany) |
| 0.50 g | dimethyl diallyl ammonium chloride/sodium acrylate/acrylamide terpolymer (Merquat ® Plus 3 330, Calgon, U.S.A.) |
| 0.25 g | copolymer of acrylic acid and acrylamide sodium salt (Hostacerin PN 73 ®, Hoechst, Germany) and |
| 3.00 g | polyvinylpyrrolidone (Luviskol ® VA 64, BASF AG, Germany) |
| 0.20 g | nonylphenol ethoxylated with 14 moles ethylene oxide |
| 0.20 g | p-hydroxybenzoic acid methyl ester |
| 0.10 g | perfume oil |
| 85.75 g | water |
| 100.00 g | |

Example 4

Gel spray with normal fixing

| | |
|---|---|
| 5.00 g | mixture of glucose disaccharide and glucose oligosaccharide (C-Pur ® 01924, Cerestar, Germany) |
| 0.50 g | diquaternary polydimethylsiloxane (Abil ® Quat 3272, Goldschmidt, Germany) |
| 1.00 g | sclerotium gum (Amigel ®, Alban Muller) |
| 0.20 g | nonylphenol ethoxylated with 14 moles ethylene oxide |
| 0.20 g | p-hydroxybenzoic acid methyl ester |
| 0.10 g | perfume oil |
| 93.00 g | water |
| 100.00 g | |

Example 5

Gel spray with normal fixing

| | |
|---|---|
| 3.00 g | maltose |
| 0.50 g | polyvinylpyrrolidone/imidazoliminmethochloride (Luviquat ® HM 550, BASF AG, Germany) |
| 0.20 g | homopolymer of acrylic acid with a molecular weight of 4,000,000 (Carbopol ® 980, B. F. Goodrich, U.S.A.) |
| 0.25 g | ammonia, 25-percent aqueous solution |
| 0.50 g | shellac |
| 0.20 g | nonylphenol ethoxylated with 14 moles ethylene oxide |
| 0.20 g | p-hydroxybenzoic acid methyl ester |
| 0.10 g | perfume oil |
| 95.05 g | water |
| 100.00 g | |

Example 6

Wet gel

| | |
|---|---|
| 3.00 g | mixture of glucose disaccharide and glucose oligosaccharide (C-Pur ® 01924, Cerestar, Germany) |
| 0.50 g | vinylpyrrolidone/dimethylaminoethyl methacrylate/vinylcaprolactum terpolymer (Gaffix ® VC 713, ISP, U.S.A.) |
| 0.25 g | homopolymer of acrylic acid with a molecular weight of 6,000,000 (Modarez ® V 600 PX, Protex, France) |
| 0.20 g | 2-amino-2-methylpropanol |
| 0.20 g | nonylphenol ethoxylated with 14 moles ethylene oxide |
| 0.10 g | perfume oil |
| 95.75 g | water |
| 100.00 g | |

Example 7

Gel spray with intensive fixing

| | |
|---|---|
| 3.00 g | maltose |
| 0.50 g | vinylpyrrolidone/methacrylamidopropyl trimethylammonium chloride copolymer (Gafquat ® HS 100, Gaf Co., U.S.A.) |
| 0.20 g | homopolymer of acrylic acid with a molecular weight of 4,000,000 (Carbopol ® 980, B. F. Goodrich, U.S.A.) |
| 1.00 g | methacrylic acid/methacrylate copolymer (Diahold ® A 503, Sandoz, Switzerland) |
| 0.50 g | hydroxypropyl chitosan |
| 0.20 g | nonylphenol ethoxylated with 14 moles ethylene oxide |
| 0.10 g | perfume oil |
| 94.50 g | water |
| 100.00 g | |

The pH of the composition is adjusted to 7.0 with aqueous sodium hydroxide solution.

Example 8

| | |
|---|---|
| 7.000 g | mixture of glucose disaccharide and glucose oligosaccharide (C-Pur ® 01924, Cerestar, Germany) |
| 0.500 g | polyvinylpyrrolidone/dimethylaminoethyl methacrylate copolymer (Gafquat ® 755 N, Gaf Co., U.S.A.) |
| 0.250 g | homopolymer of acrylic acid with a molecular weight of 4,000,000 (Carbopol ® 980, B. F. Goodrich, U.S.A.) |
| 0.290 g | 2-amino-2-methylpropanol |
| 0.200 g | hydrated castor oil ethoxylated with 45 moles ethylene oxide |
| 0.200 g | cetyl/stearyl alcohol alkoxylated with 9 moles ethylene oxide and 2 moles propylene oxide |

-continued

| | |
|---|---|
| 1.800 g | p-hydroxybenzoic acid methyl ester |
| 0.180 g | Basic Red 76 (C.I. 12,245) |
| 0.015 g | Basic Violet 14 (C.I. 42,510) |
| 0.230 g | 1-N-hydroxyethylamino-4-methyl-2-nitrobenzene |
| 0.300 g | 1,4-bis(2-hydroxyethyl)amino-2-nitro-5-chlorobenzene |
| 0.200 g | perfume oil |
| 88.835 g | water |
| 100.00 g | |

Example 9

| | |
|---|---|
| 7.0000 g | mixture of glucose disaccharide and glucose oligosaccharide (C-Pur ® 01924, Cerestar, Germany) |
| 0.5000 g | polyvinylpyrrolidone/dimethylaminoethyl methacrylate copolymer (Gafquat ® 755 N, Gaf Co., U.S.A.) |
| 0.2500 g | homopolymer of acrylic acid with a molecular weight of 4,000,000 (Carbopol ® 980, B. F. Goodrich, U.S.A.) |
| 0.2900 g | 2-amino-2-methylpropanol |
| 0.2000 g | hydrated castor oil ethoxylated with 45 moles ethylene oxide |
| 0.2000 g | cetyl/stearyl alcohol alkoxylated with 9 moles ethylene oxide and 2 moles propylene oxide |
| 1.8000 g | p-hydroxybenzoic acid methyl ester |
| 0.0300 g | 1-N-hydroxyethylamino-4-methyl-2-nitrobenzene |
| 0.0035 g | 1,4-bis(2-hydroxyethyl)amino-2-nitro-5-chlorobenzene |
| 0.2000 g | perfume oil |
| 89.5265 g | water |
| 100.00 g | |

All percentages indicated in the present Application represent percent by weight.

We claim:

1. An aqueous hair fixing composition in the form of a sprayable gel and containing
    0.1 to 50 percent by weight of at least one disaccharide or 0.1 to 50 percent by weight of a mixture of 2 to 37 percent by weight of at least one disaccharide and 63 to 98 percent by weight of at least one oligosaccharide,
    0.05 to 30 percent by weight of at least one cationic polymer,
    0.05 to 10 percent by weight of at least one thickener selected from the group consisting of homopolymers of acrylic acid, acrylic acid/acrylamides copolymers and sclerotium gum,
    no monovalent aliphatic alcohols having 1 to 4 carbon atoms,
    no inorganic salts of alkali metals, bivalent metals or trivalent metals; and
    a gaseous propellant.

2. The composition as defined in claim 1, and free of organic solvents.

3. The composition as defined in claim 1, wherein said mixture contains glucose disaccharides as said at least one disaccharide and glucose oligosaccharides as said at least one oligosaccharide.

4. The composition as defined in claim 3, containing maltose as said at least one disaccharide.

5. The composition as defined in claim 1, containing 1 to 25 percent by weight of said at least one disaccharide or said mixture.

6. The composition as defined in claim 1, containing a polyvinylpyrrolidone/dimethylaminoethyl methacrylate copolymer, a copolymer of polyvinylpyrrolidone and imidazoliminmethochloride, a dimethyldiallyl ammonium chloride/sodium acrylate/acrylamide terpolymer, a terpolymer of vinylpyrrolidone, dimethylaminoethyl methacrylate and vinylcaprolactum, a quaternary ammonium salt of hydroxyethylcellulose and a trimethylammonium-substituted epoxide, a vinylpyrrolidone/methacrylamidopropyltrimethyl ammonium copolymer or a diquaternary polydimethylsiloxane as said at least one cationic polymer.

7. The composition as defined in claim 1, containing from 0.05 to 10 percent by weight of said at least one cationic polymer.

8. The composition as defined in claim 1, wherein said at least one thickener consists of at least one of said hozopolyzers of said acrylic acid having an average molecular weight of 4,000,0000.

9. The composition as defined in claim 1, wherein said at least one thickener consists of at least one of said homopolymers of said acrylic acid having an average molecular weight of 2,000,000 to 6,000,000.

10. The composition as defined in claim 1, containing from 0.1 to 5 percent by weight of said at least one thickener.

11. The composition as defined in claim 1, further comprising from 0.1 to 15 percent by weight of a nonionic polymer.

12. The composition as defined in claim 1, further comprising from 0.1 to 15 percent by weight of an anionic polymer.

13. The composition as defined in claim 1, wherein said gaseous propellant is at least one member selected from the group consisting of $N_2$, $N_2O$, $CO_2$, n-butane, i-butane and propane.

14. The composition as defined in claim 1, wherein said gaseous propellant is a lower alkane or mixture of said loper alkane with dinethyl ether.

15. An aqueous h air fixing composition in the form of a sprayable gel and containing
    0.1 to 50 percent by weight of at least one disaccharide or 0.1 to 50 percent by weight of a mixture of 2 to 37 percent by weight of at least one disaccharide and 63 to 98 percent by weight of at least one oligosaccharide,
    0.05 to 30 percent by weight of at least one cationic polyimer,
    0.05 to 10 percent by weight of at least one thickener selected from the group consisting of homopolymers of acrylic acid, acrylic acid/acrylamides copolymers and sclerotium gum,
    no monovalent aliphatic alcohols having 1 to 4 carbon atoms, and
    no inorganic salts of alkali metals, bivalent metals or trivalent metals; and
    a mechanical spray device for the aqueous hair fixing composition.

16. The composition and mechanical spray device as defined in claim 15, wherein the composition is free of organic solvents.

17. The composition and mechanical spray device as defined in claim 15, wherein said mixture contains glucose disaccharides as said at least one disaccharide and glucose oligosaccharides as said at least one oligosaccharide.

18. The composition and mechanical spray device as defined in claim 15, wherein the composition contains maltose as said at least one disaccharide.

19. The composition and mechanical spray device as defined in claim 15, wherein the composition contains 1 to 25 percent by weight of said at least one disaccharide or said mixture.

20. The composition and mechanical spray device as defined in claim 1, wherein the composition contains a polyvinylpyrrolidone/dimethylaminoethyl methacrylate copolymer, a copolymer of polyvinylpyrrolidone and imidazoliminmethochloride, a dimethyldiallyl ammonium chloride/sodium acrylate/acrylamide terpolymer, a terpolymer of vinylpyrrolidone, dimethylaminoethyl methacrylate and vinylcaprolactum, a quaternary ammonium salt of hydroxyethylcellulose and a trimethylammonium-substituted epoxide, a vinylpyrrolidone/methacrylamidopropyltrimethyl ammonium copolymer or a diquaternary polydimethylsiloxane as said at least one cationic polymer.

21. The composition and mechanical spray device as defined in claim 15, wherein composition contains from 0.05 to 10 percent by weight of said at least one cationic polymer.

22. The composition and mechanical spray device as defined in claim 15, wherein said at least one thickener consists of one of said homopolyzers of said acrylic acid having an average molecular weight of 4,000,000.

23. The composition and mechanical spray device as defined in claim 15, wherein said at least one thickener consists of one of said homopolymers of said acrylic acid having an average molecular weight of 2,000,000 to 6,000,000.

24. The composition and mechanical spray device as defined in claim 14, wherein the composition contains from 0.1 to 5 percent by weight of said at least one thickener.

25. The composition and mechanical spray device as defined in claim 14, wherein the composition includes from 0.1 to 15 percent by weight of a nonionic polymer.

26. The composition and mechanical spray device as defined in claim 14, wherein the composition includes from 0.1 to 15 percent by weight of an a nonionic polymer.

27. The composition and mechanical spray device as defined in claim 14, wherein said mechanical spray device is a spray pump or a flexible container provide with a spray valve.

28. An aqueous hair fixing composition in the form of a sprayable gel and containing 0.1 to 50 percent by weight of at least one disaccharide or 0.1 to 50 percent by weight of a mixture of 2 to 37 percent by weight of at least one disaccharide and 63 to 98 percent by weight of at least one oligosaccharide, 0.05 to 10 percent by weight of at least one cationic polymer selected from the group consisting of polyvinylpyrrolidone/dimethylaminoethylmethacrylate copolymers; copolymers of polyvinylpyrrolidone and imidazoliminmethochloride; dimethyldiallyl ammonium chloride/sodium acrylate/acrylamide terpolymers; terpolymers of vinylpyrrolidone, dimuethylaminoethyl methacrylate and vinylcaprolactum; quaternary ammonium salts of hydroxyethylcellulose and a trimethylammonium-substituted epoxide; vinylpyrrolidone/methacrylamidopropyltrimethyl ammonium copolymers and diquaternary polydimethylsiloxane, 0.05 to 10 percent by weight of at least one homopolymers of acrylic acid having a molecular weight between 2,000,000 and 4,000,000, 50 to 96 percent by weight water, no monovalent aliphatic alcohols having 1 to 4 carbon atoms, and no inorganic salts of alkali metals, bivalent metals or trivalent metals; and a mechanical spray device for the aqueous hair fixing composition.

29. The aqueous hair fixing composition and mechanical spray device as defined in claim 27, wherein said at least one disaccharide consists of maltose.

* * * * *